Figure 1:
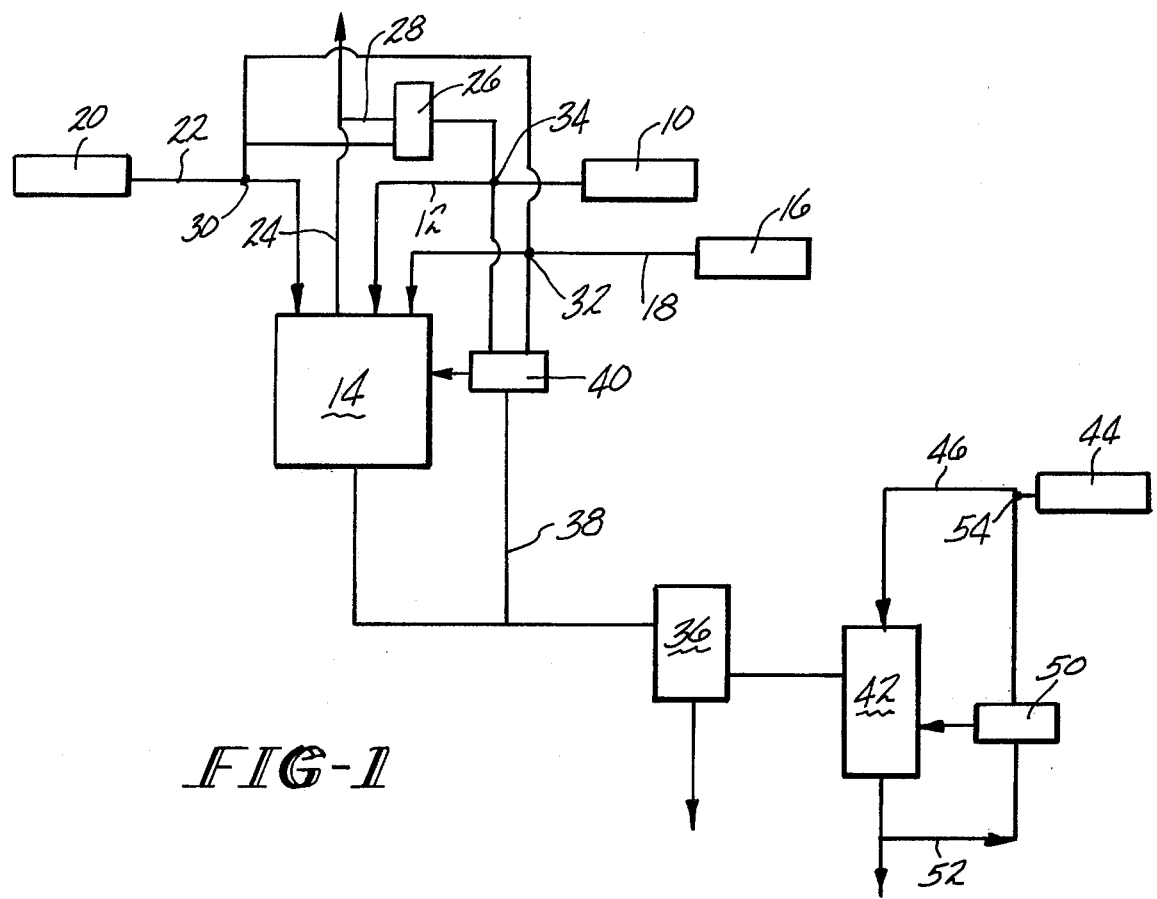

United States Patent [19]

Capuano

[11] 4,162,897

[45] Jul. 31, 1979

[54] METHOD OF MEASURING NITROGEN TRICHLORIDE IN A PROCESS FOR THE SAFE PRODUCTION OF POLYCHLOROISOCYANURATES

[75] Inventor: Italo A. Capuano, Orange, Conn.

[73] Assignee: Olin Corporation, New Haven, Conn.

[21] Appl. No.: 834,939

[22] Filed: Sep. 20, 1977

Related U.S. Application Data

[62] Division of Ser. No. 744,489, Nov. 24, 1976, Pat. No. 4,087,607.

[51] Int. Cl.$^2$ .............................................. G01N 31/08
[52] U.S. Cl. ................................ 23/232 C; 23/230 A
[58] Field of Search ........................... 23/232 C, 230 A; 73/23.1; 55/67, 197, 386

[56] References Cited

U.S. PATENT DOCUMENTS

3,167,946   2/1965   Broerman et al. .................. 55/67 X

OTHER PUBLICATIONS

Pappas et al., Anal. Chem. 40, 2176 (1968).
Spears et al., Gas Chromat. Abstr., 1969, #524.

*Primary Examiner*—R. E. Serwin
*Attorney, Agent, or Firm*—James B. Haglind; Donald F. Clements

[57] ABSTRACT

Polychloroisocyanurate products are produced in a continuous process which reacts a cyanuric acid component with a chlorinating agent in a reaction mixture to which a purge gas is fed to remove in an effluent gas, any nitrogen trichloride produced along with other by-products. The effluent gas is fed to a gas analyzer such as a gas chromatograph which determines the concentration of $NCl_3$ present and compares it with a predetermined upper limit. If this upper limit is equalled or exceeded, the gas analyzer activates means to flood the reaction mixture with purge gas to prevent explosive amounts of nitrogen trichloride from being present in the reaction mixture. The gas analyzer may also control the feed rate of the cyanuric acid component and the chlorinating agent.

The pH of the reaction mixture is also continuously measured in a pH analyzer having means to control the flow rate of the purge gas and reactants should the predetermined pH limits for the reaction be attained or exceeded.

Also, the available chlorine concentration of a cyanuric acid containing effluent from a stripping unit is determined by an available halogen monitor which controls the feeding of acid to the stripper and prevents contamination of the effluent.

A safe, non-polluting process is provided which greatly reduces the risk of an explosion because of the formation of nitrogen trichloride.

4 Claims, 2 Drawing Figures

METHOD OF MEASURING NITROGEN TRICHLORIDE IN A PROCESS FOR THE SAFE PRODUCTION OF POLYCHLOROISOCYANURATES

This is a division of application Ser. No. 744,489, filed Nov. 24, 1976, now U.S. Pat. No. 4,087,607.

This invention relates to an improved process for the production of polychloroisocyanurate products by the chlorination of a cyanuric acid component. Polychloroisocyanurates are well known products used in washing, bleaching and sanitizing applications.

It is known to react cyanuric acid or an alkali metal cyanurate with a chlorinating agent such as hypochlorous acid or chlorine to produce polychloroisocyanurates. Suitable processes are described, for example, in U.S. Pat. No. 2,956,056 issued to Christian; U.S. Pat. No. 2,964,525, issued to Robinson; U.S. Pat. No. 3,712,891 issued to Berkowitz and Mesiah; U.S. Pat. No. 3,835,134 issued to Schiessl, Sawhill and Bhutani; and U.S. Pat. No. 3,835,135 issued to Sawhill.

In each of the above processes there is inherent the danger of producing explosive amounts of nitrogen trichloride as a by-product. This danger is well known and various procedures, including the use of a gas such as nitrogen or chlorine to purge nitrogen trichloride from the reaction mixture, have been employed.

However, in the known processes for polychloroisocyanurate products, there is no teaching of accurate methods for the continuous determination of nitrogen trichloride nor for means for process control responding to the analyses.

Therefore, it is an object of the present invention to provide a non-hazardous process for the production of polychloroisocyanurate products.

A further object of the present invention is a process in which the presence of explosive amounts of by-product nitrogen trichloride is prevented.

An additional object of the present invention is an accurate method of analysis for nitrogen trichloride.

These and other objects of the invention will be apparent from the following description of the invention.

Briefly, in a continuous process for producing a polychloroisocyanurate product by reacting a liquid containing a cyanuric acid component with a chlorinating agent at a temperature of from about $-5°$ to about $45°$ C. to produce a liquid reaction mixture containing a polychloroisocyanurate product and any by-product nitrogen trichloride obtained, the improvement which comprises:

(a) supplying the liquid containing cyanuric acid component through flow control means into a reactor, (b) supplying the chlorinating agent through flow control means into the reactor, (c) passing a purge gas through flow control means to the reactor to admix with the reaction mixture to form an effluent gas, (d) removing the effluent gas from the reactor, (e) introducing a portion of the effluent gas into a gas analyzer, (f) determining the nitrogen trichloride concentration in the effluent gas, (g) recording the concentration of nitrogen trichloride on a recording device, (h) providing the recording device with an upper limit for the concentration of nitrogen trichloride in the effluent gas, (i) comparing the upper limit with the recorded concentration of nitrogen trichloride of step g, and (j) activating the flow control means for the purge gas to increase the flow of purge gas to the reactor when said recorded concentration equals or exceeds said upper limit.

Figure 2:
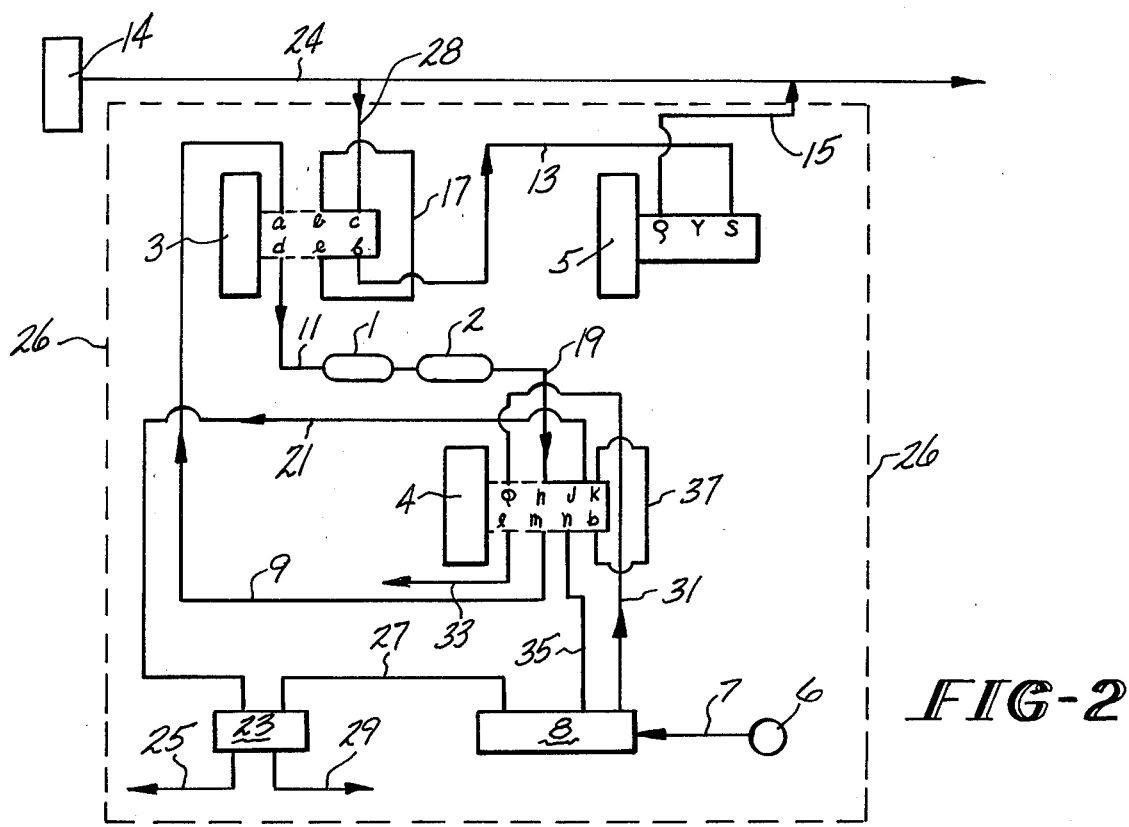

The improved process of the present invention is further illustrated by accompanying FIGS. 1-2. Corresponding parts have the same numbers in both Figures.

FIG. 1 presents a flow diagram of the improved process of the present invention.

FIG. 2 illustrates a schematic view of the gas analyzer employed in the improved process of the present invention.

In the flow diagram of FIG. 1, a chlorinating agent is fed from tank 10 thru line 12 to reactor 14. Simultaneously, an aqueous slurry of a cyanuric acid component is introduced to reactor 14 from tank 16 thru line 18. Also fed from tank 20 to reactor 14 thru line 22 is a purge gas. Vaporizable by-products produced during the chlorination reaction in reactor 14 are removed thru pipe 24. A sample of the gaseous products is continuously introduced into gas analyzer 26 thru pipe 28. The gas is analyzed and the concentration of any nitrogen trichloride present determined. Should an excessive amount of nitrogen trichloride be detected, gas analyzer 26 activates valve 30 in line 22 to increase the flow of purge gas to reactor 14. At the same time, gas analyzer 26 may activate valve 32 in line 18 to reduce or stop the flow of the cyanuric acid component to reactor 14, and valve 34 in line 12 may be activated by gas analyzer 26 to change the flow of the chlorinating agent to reactor 14. The increased flow of purge gas dilutes the concentration of nitrogen trichloride in the gaseous products. When the concentration of nitrogen trichloride is reduced to within the permitted range, valve 30 is activated to restore the purge gas flow to the desired level.

An aqueous solution or slurry of a polychloroisocyanurate product is removed from reactor 14 and fed to filter 36. A portion of the slurry is recirculated to reactor 14 thru line 38. A sample of the aqueous product is continuously introduced to pH analyzer 40. Should the pH of the aqueous product exceed the predetermined limit, pH analyzer 40 activates valve 30 to increase the flow of purge gas in line 22, and valves 34 and 32 may be activated to change the flow of the cyanuric acid component and the chlorinating agent to reactor 14.

The filtered polychloroisocyanurate product is removed from filter 36 and sent to storage. The filtrate is pumped to stripper 42 in which it is mixed with an acid fed from tank 44 thru line 46. Following acidification, the effluent is discharged from stripper 42 thru line 48. A portion of the effluent from line 48 is recirculated to stripper 42 thru line 52 in which available halogen monitor 50 is installed. Available halogen monitor 50 determines the concentration of available chlorine in the effluent and when it exceeds a predetermined limit, activates valve 54 in line 46 to increase the flow of mineral acid to stripper 42.

Gas analyzer 26 is illustrated schematically in FIG. 2. Analyzer 26 includes conventional chromatographic columns 1 and 2 which are identically filled with a partitioning material capable of separating nitrogen trichloride from the effluent gases from chloroisocyanurate reactor 14. Gas analyzer 26 includes three stream switching valves 3, 4 and 5. Valve 3 is provided with six ports 3a, 3b, 3c, 3d, 3e and 3f. A sample of the effluent gases in pipe 24 continuously enters valve 3 via line 28 thru port 3c.

A carrier gas, such as helium, is introduced into the system through line 7 from tank 6. It passes through manifold 8 to valve 4 via line 35. Valve 4 has eight ports 4g, 4h, 4j, 4k, 4l, 4m, 4n, and 4p with the carrier gas entering at port 4n. The carrier gas passes through port 4m of valve 4 and enters valve 3 through port 3a which communicates with line 9. From port 3a of valve 3 the carrier gas flows through port 3d via line 11 to columns 1 and 2. Columns 1 and 2 are filled with polytetrafluoroethylene powder having a surface coating of a silicone oil as the partition liquid.

In operation, the effluent gases entering port 3c of valve 3 pass through port 3b and into sample loop 17. The effluent gases re-enter valve 3 at port 3e and pass through port 3f to enter line 13 which communicates with port 5s of valve 5. The effluent gases leave valve 5 through port 5q and return through conduit 15 to pipe 24.

When it is desired to perform an analysis of the effluent gases, valve 5 is closed to prevent the flow of the effluent gases into conduit 15. A fixed volume of effluent gas is trapped in sample loop 17. Valve 3 is activated so that the carrier gas passes from port 3a to port 3b where it purges the fixed volume of effluent gases contained in sample loop 17 to columns 1 and 2 via ports 3e and 3d. The gaseous mixture is fed through columns 1 and 2 where separation of any nitrogen trichloride in the effluent gases takes place. After passing through the column, the separated components enter port 4h of valve 4 through line 19. The components leave valve 4 through port 4j and are fed to detector 23 through line 21. In the detector the concentration of any nitrogen trichloride present is detected and recorded, along with the concentration of any other desired components, and the gases vented through line 25. Carrier gas is also fed to detector 23 from manifold 8 via line 27 and is vented through line 29.

Activation of valve 4 allows carrier gas to pass thru line 31 to enter port 4g, exit thru port 4h and flow countercurrent through columns 2 and 1 to ports 3d and 3a of valve 3. From valve 3 the carrier gas enters port 4m of valve 4 and leaves port 4l to be vented thru line 33. Simultaneously, carrier gas entering port 4n thru line 35 is passed thru port 4p into loop 37 to port 4k and leaves valve 4 at port 4j to be fed to detector 23 thru line 21. By this procedure, columns 1 and 2 are cleaned out and readied for the next analysis.

In the improved process of the present invention, one of the reactants is a liquid containing a cyanuric acid component. Suitable cyanuric acid components include cyanuric acid, alkali metal cyanurates such as monosodium cyanurate, disodium cyanurate and trisodium cyanurate, and alkaline earth metal cyanurates. The cyanuric acid component is normally supplied to the reactor as a solution or slurry in water although other solvents such as aliphatic liquid chlorinated hydrocarbons, including carbon tetrachloride, chloroform, 1,1- and 1,2-dichloroethane, and propyl chloride, may be used as the liquid.

Suitable chlorinating agents for use in the present process include hypochlorous acid, alkali metal hypochlorites, chlorine, dichlorine monoxide and mixtures thereof.

The reactants are fed to the reactor thru flow control means such as valves in suitable proportions to produce the desired polychloroisocyanurate product. For example, when a monoalkali metal cyanurate is the cyanuric acid component and hypochlorous acid is the chlorinating, a molar ratio of hypochlorous acid to monoalkali metal cyanurate of from about 1:1 to about 1.1:1 is maintained to produce dichloroisocyanuric acid. Where trichloroisocyanuric acid is the desired product, a molar ratio of hypochlorous acid to monoalkali metal cyanurate of from about 2:1 to about 2.2:1 is maintained.

In addition to the above reactants, a purge gas is fed to the reactor thru control means to remove any by-products which might be formed. By-products which can be formed during the reaction include nitrogen trichloride, carbon dioxide, nitrogen, ammonia and water vapor.

Of primary concern is the possible build up of nitrogen trichloride as it can be explosively dangerous. $NCl_3$ is normally present in the liquid form when the reaction temperature is kept below 50° C. To prevent this build up, the purge gas fed to the reaction mixture vaporizes any nitrogen trichloride present and the mixture is removed from the reactor as an effluent gas.

Any of several gases can be employed as the purge gas including, chlorine, nitrogen and air, chlorine is a preferred purge gas as it can also be employed as a chlorinating agent.

The effluent gas removed from the reactor is conducted to a scrubbing unit containing an aqueous solution of an alkali metal compound such as a carbonate or hydroxide. In the scrubbing unit, any nitrogen trichloride present is decomposed to nitrogen and chlorine and all chlorine present reacts with the alkali metal compound to form an alkali metal hypochlorite. The alkali metal hypochlorite may be fed to the reactor as a chlorinating agent or it may be further reacted with additional chlorine to produce a hypochlorous acid solution.

Prior to being fed to the scrubbing unit, a portion of the exhaust gas is fed to gas analyzer 26. As described above, the gas analyzer is a single stream process gas chromatograph which contains chromatographic columns which separate any nitrogen trichloride present from other components in the effluent gas. The gas analyzer is programmed to periodically select and analyze a sample of the effluent gas. Where nitrogen trichloride is present, its concentration is measured and recorded on a recording device such as a meter. The recording device is also provided with an upper limit for the concentration of nitrogen trichloride permitted in the effluent gas. Should the nitrogen trichloride concentration in the sample analyzed exceed this upper limit, for example, a concentration of about 1.0 percent by volume of $NCl_3$, a contact in the recording device activates an alarm or the flow control means (e.g. a solenoid valve) in line 20. As a result, the flow of purge gas to the reactor is increased to dilute $NCl_3$ concentration in the reactor. When subsequent analyses show reduced concentrations of nitrogen trichloride in the effluent gas, the valve is activated to reduce the flow of purge gas in line 20.

In a preferred embodiment, the detector in the gas analyzer employs cells for measuring the thermal conductivity of the components in the effluent gases and the carrier gas is helium or hydrogen.

To provide additional insurance of a non-hazardous process, the polychloroisocyanurate product stream being continuously removed from the reactor is monitored by pH analyzer 40. A portion of the product stream which is to be filtered is circulated through line 38 to pH analyzer 40 and the stream returned to reactor 14. The pH analyzer is programmed to continuously measure the pH of the product stream and provide the result to a recording device. The recording device is also provided with predetermined limits which are selected with respect to the desired polychloroisocyanurate product. Where the product stream is trichloroisocyanuric acid, it is important to prevent the pH from rising above a predetermined upper limit of about 3.2. When sodium dichloroisocyanurate is produced, the recorder is provided with both an upper limit of about 6.6 and a lower limit of about 6.4. When this limit is attained or exceeded, a contact on the recording device of the pH analyzer activates valve 30 in line 22 to increase the flow of purge gas to reactor 14. An alarm may also be energized to appraise operating personnel of the condition of the reaction mixture. The pH analyzer may also be programmed to activate valve 34 in line 12 to change the flow rate of the chlorinating agent and valve 32 in line 18 to alter the flow rate of the cyanuric acid component.

pH analyzer 40 may be any instrument which is capable of continuously monitoring the product stream and suitably includes a sampling unit, a measuring cell and a recording device and may have self-standardizing capabilities.

After removal from reactor 14, the polychloroisocyanurate product stream is fed to filter 36 where the polychloroisocyanurate product is separated from a mother liquor. The mother liquor is normally an aqueous solution containing some dissolved polychloroisocyanurate product and may also contain dissolved alkali metal chloride. After being fed to stripper 42, the mother liquor is acidified to release the available chlorine from any polychloroisocyanurate product present. Any acid having an ionization constant larger than that of cyanuric acid can be employed. It is preferred to use a mineral acid such as hydrochloric acid, sulfuric acid, phosphoric acid or nitric acid. A sufficient amount of acid is added to react with substantially all chlorine which is chemically combined in the isocyanurate structure. A suitable process for recovering chlorine values from polychloroisocyanurates is disclosed in U.S. Pat. No. 3,835,136, issued to L. C. Hirdler, H. W. Schiessl and D. F. Doonan. The disclosure of this patent is incorporated by reference herein.

It is desired that the effluent stream from stripper 42 be an available chlorine-depleted slurry of cyanuric acid which may contain varying amounts of an alkali metal chloride. To insure that the effluent stream is deplete of available chlorine, a portion of the effluent stream is passed through available halogen monitor 50 and recycled to stripper 42. Any free available chlorine present in the effluent stream is detected by the available halogen monitor 50 which has means for activating valve 54 in line 46 to increase the flow of acid to stripper 42.

Any available halogen monitor may be used which is capable of determining available chlorine concentrations of about 0.1% or less. A preferred monitor is that disclosed in U.S. Pat. No. 3,956,094 issued to I. A. Capuano. The disclosure of this patent is incorporated by reference herein.

In addition to monitoring the chlorination reactor in the production of a polychloroisocyanurate product, the gas analyzer for nitrogen trichloride may be employed in other operations where polychloroisocyanurate product decomposition may occur resulting in the formation of $NCl_3$. Examples of these operations include the drying of polychloroisocyanurate products in dryers such as spray dryers or fluidized, bed dryers, and in equipment such as compactors or crushers where the particle size of the polychloroisocyanurate product is reduced for example, by grinding. In both of these operations, thermal decomposition of the polychloroisocyanurate product may occur resulting in the formation of excessive amounts of nitrogen trichloride thus creating an explosive hazard.

What is claimed is:

1. A method of analyzing effluent gases from a polychloroisocyanurate product for nitrogen trichloride which comprises:
    (a) introducing said effluent gases into a first zone,
    (b) introducing a carrier gas into said first zone to form a gaseous mixture,
    (c) passing said gaseous mixture from said first zone through a chromatographic column to separate said nitrogen trichloride from said gaseous mixture,
    (d) passing said nitrogen trichloride from said chromatographic column to a detector to measure the concentration of said nitrogen trichloride from said chromatographic column,
    (e) recording said concentration of nitrogen trichloride on a recording device,
    (f) providing said recording device with an upper limit for the concentration of nitrogen trichloride in said effluent gases, and
    (g) activating an alarm when said upper limit of said concentration is reached or exceeded.

2. The method of claim 1 in which said detector employs means for measuring thermal conductivity of said nitrogen trichloride.

3. The method of claim 2 in which said carrier gas is helium or hydrogen.

4. The method of claim 3 in which said chromatographic column contains polytetrafluoroethylene powder coated by a silicone oil.

* * * * *